United States Patent [19]

Ishikawa et al.

[11] Patent Number: 5,640,221
[45] Date of Patent: Jun. 17, 1997

[54] BINOCULAR OPTICAL IMAGE-PICKUP EQUIPMENT AND BINOCULAR IMAGE-PICKUP SYSTEM

[75] Inventors: Norio Ishikawa; Hidehiro Hosaka; Katsumi Nakaichi, all of Tokyo, Japan

[73] Assignee: Nihon Kohden Corporation, Tokyo, Japan

[21] Appl. No.: 647,831

[22] Filed: May 15, 1996

[30] Foreign Application Priority Data

May 15, 1995 [JP] Japan ................... 7-115847

[51] Int. Cl.$^6$ ................... A61B 3/10; A61B 3/00
[52] U.S. Cl. ................... 351/221; 351/200; 351/205
[58] Field of Search ................... 351/203, 200, 351/205, 206, 221, 246; 359/407, 419

[56] References Cited

U.S. PATENT DOCUMENTS

| | | | |
|---|---|---|---|
| 3,535,026 | 10/1970 | Coss | 351/1 |
| 4,568,153 | 2/1986 | Baluteau | 359/407 |
| 4,702,575 | 10/1987 | Breglia | 351/210 |
| 4,712,895 | 12/1987 | Kamiyama et al. | 351/243 |

FOREIGN PATENT DOCUMENTS

| | | | |
|---|---|---|---|
| 8604799 | 8/1986 | WIPO | A61B 3/10 |
| 9205736 | 4/1992 | WIPO | A61B 3/02 |

OTHER PUBLICATIONS

Scinto et al, A Potential Noninvasive Neurobiological Test for Alzheimer's Disease, Nov. 11, 1994, vol. 266 pp. 1051-1054.

Patent Abstracts of Japan, vol. 95, No. 004 & JP-A-07 100146 (Kazumi Makishima; Others: 01) Apr. 18. 18, 1995, * abstract.

*Primary Examiner*—Hung X. Dang
*Attorney, Agent, or Firm*—Sughrue, Mion, Zinn, Macpeak & Seas

[57] ABSTRACT

A housing has a hollow section, and openings are formed at both ends of the hollow section so as to communicate with the outside. An aperture is formed in the internal wall of the housing so as to oppose the opening, and a video camera is fitted into the opening. A half mirror, a mirror, an optical lens, and light sources are disposed within the hollow section. The light sources are alternately illuminated while a patient wears equipment having such a construction. Light reflected from one eye passes through the half mirror and enters a light receiving surface of the video camera. On the other hand, light reflected from the other eye is reflected from the mirror and a half mirror and, then, enters the light receiving surface of the video camera. The optical lens corrects an error arising from a difference in length between two optical paths.

8 Claims, 5 Drawing Sheets

FIG. 4(a) — CLOSE / OPEN

FIG. 4(b) — INDICATE / TURN OFF

FIG. 4(c) — INDICATE / TURN OFF

LEFT  RIGHT  LEFT
LEFT  RIGHT  LEFT

1/60 SECOND
1 FIELD

BINOCULAR OPTICAL IMAGE-PICKUP EQUIPMENT AND BINOCULAR IMAGE-PICKUP SYSTEM

BACKGROUND OF THE INVENTION

1. Field of the invention

The present invention relates to binocular optical image pick-up equipment and an image pick-up system.

2. Related Art

Conventional binocular image pick-up equipment used in measuring eye movement and a pupil diameter is provided with video cameras for use with the respective right and left eyes.

Such a construction renders the conventional binocular image pick-up equipment bulky and heavy as a whole, and resultantly expensive. It recently became evident that the measurement of changes in the pupil diameter caused as a result of dropping a pupil-dilating agent into an eye of the patient enables the diagnosis of Alzheimer's disease (SCIENCE, VOL 266, 11 Nov., 1994). It takes a long time to measure the pupil diameter for the diagnosis of Alzheimer's disease. However, as previously mentioned, the conventional binocular image pick-up equipment was bulky and heavy, and hence it was impossible for the patient to wear the equipment for a long period of time.

SUMMARY OF THE INVENTION

The present invention is conceived to solve the drawbacks in the related art, and the primary object of the present invention is to provide inexpensive light-weight compact binocular image pick-up equipment and to implement the measurement of a pupil diameter over a long period of time.

According to a first aspect of the present invention, there is provided binocular optical image pick-up equipment comprising:

a pair of light sources;

a support member for supporting the pair of light sources;

a video camera which is disposed close to one of the pair of light sources and is attached to the support member;

a mirror disposed close to the other one of the light sources for reflecting light entering in parallel with the light axis of the video camera so as to travel forward of a front light-receiving surface of the video camera;

a half mirror disposed forward of the video camera which permits light entering along the light axis of the video camera to transmit but reflects the light reflected from the mirror so as to enter the light receiving-surface of the video camera; and a magnifying or reducing lens disposed in at least one of an optical path which enters the half mirror from a forward position at a predetermined distance along the light axis of the video camera and an optical path which enters the mirror from a forward position at a predetermined distance along the optical axis in parallel with the light axis of the video camera and then enters the half mirror, the magnifying or reducing lens correcting an optical error arising from a difference in length between the two optical paths, that is, a difference in the size of images formed on the light receiving surface of the video camera.

According to a second aspect of the present invention, there is provided a binocular image pick-up system comprising the binocular optical image pick-up equipment as defined in the first aspect of the present invention;

light source drive means for driving the pair of light sources; and video camera control means for alternately illuminating the pair of light sources by activating the light source drive means, as well as for controlling the video camera in synchronism with the periodicity of the illumination.

According to a third aspect of the present invention, there is provided a binocular optical image pick-up equipment comprising:

the elements which are the same as those of the binocular optical image pick-up equipment as defined in the first aspect of the present invention except that the mirror is a first half mirror, and the half mirror is a second half mirror;

a first opening for transmitting light entering forward of the video camera and the second half mirror along the light axis of the video camera;

a second opening for transmitting light entering forward of the first half mirror along the optical axis in parallel with the light axis of the video camera;

a third opening for transmitting light so as to enter the first half mirror from the rear side thereof; and a cover for preventing the entry of external light into the two optical paths and the optical path connecting between the third opening and the first half mirror from outside other than through the first to third openings.

According to a fourth aspect of the present invention, there is provided a binocular image pick-up system comprising the binocular optical image pick-up equipment as defined in the third aspect of the present invention;

light source drive means for driving the pair of light sources; and video camera control means for alternately illuminating the pair of light sources by activating the light source drive means, as well as for controlling the video camera in synchronism with the periodicity of the illumination.

According to a fifth aspect of the present invention, there is provided binocular optical image pick-up equipment comprising the elements which are the same as those of the binocular optical image pick-up equipment as defined in the first aspect of the present invention;

a first opening for transmitting light entering forward of the video camera and the half mirror along the light axis of the video camera;

a second opening for transmitting light entering forward of the mirror along the optical axis in parallel with the light axis of the video camera;

a cover for preventing the entry of external light into the two optical paths from outside other than through the first and second openings; and an eye stimulating light source disposed in the cover so as to illuminate at least one of the first and second openings.

According to a sixth aspect of the present invention, there is provided a binocular image pick-up system comprising the binocular optical image pick-up equipment as defined in the fifth aspect of the present invention;

light intensity instructing means for instructing the intensity of the light originated from the eye illuminating light source;

eye illuminating light source drive means for activating the eye stimulating light source in response to an instruction from the light intensity instructing means;

photographing light source drive means for activating the pair of light sources; and video camera control means for alternately illuminating the pair of light sources by activating the light source drive means, as well as for controlling the video camera in synchronism with the periodicity of the illumination.

According to a seventh aspect of the present invention, the binocular optical image pick-up equipment, as defined in the fifth aspect of the present invention, is characterized in that the mirror is a half mirror, and the eye stimulating light source is positioned behind the half mirror with respect to the second opening.

According to an eighth aspect of the present invention, the binocular image pick-up system, as defined in the sixth aspect of the present invention, is characterized in that the mirror is a half mirror, and the eye stimulating light source is positioned behind the half mirror in parallel with the light axis of the video camera.

By virtue of the binocular optical image pick-up equipment as defined in the first aspect of the present invention, when the patient wears the equipment, one eye is positioned in front of the half mirror along the light axis of the video camera, and the other eye is positioned in front of the mirror along the light axis in parallel with the light axis of the video camera. One light source illuminates one eye, and the light reflected from the eye enters the light receiving surface of the video camera after having passed through the half mirror. The other light source illuminates the other eye, and the light reflected from the eye enters the light receiving surface after having been reflected from the mirror and the half mirror in that order. The optical lens corrects an optical error arising from a difference between the two optical paths connecting between the eyes and the light receiving surface of the video camera, i.e., a difference in the size of the images formed on the light receiving surface of the video camera.

By virtue of the binocular image pick-up system as defined in the second aspect of the present invention, the video camera control means alternately illuminates the pair of light sources by alternately activating the light source drive means, as well as controlling the video camera in synchronism with the periodicity of the illumination. As a result of this, the image signals of the right and left eyes are alternately output from the video camera.

By virtue of the binocular optical image pick-up equipment as defined in the third aspect of the present invention, when the patient wears the equipment, one eye is positioned at the first opening forward of the second half mirror along the light axis of the video camera, and the other eye is positioned at the second opening forward of the mirror along the light axis in parallel with the light axis of the video camera. One light source illuminates one eye, and the light reflected from the eye enters the light receiving surface of the video camera after having passed through the second half mirror. The other light source illuminates the other eye, and the light reflected from the eye enters the light receiving surface after having been reflected from the first half mirror and the second half mirror in that order. The optical lens corrects an optical error arising from a difference between the two optical paths connecting between the eyes and the light receiving surface of the video camera, i.e., a difference in the size of the images formed on the light receiving surface of the video camera. The video camera converts the light received by the light receiving surface into a video signal, and the thus converted video signal is output. The binocular optical image pick-up equipment allows stimulation of the other eye by illuminating it from outside via the third opening and the first half mirror.

Similar to the binocular image pick-up system as defined in the second aspect, by virtue of the binocular image pick-up system as defined in the fourth aspect of the present invention, the video signals of the right and left eyes are alternately output from the video camera.

By virtue of the binocular optical image pick-up equipment as defined in the fifth aspect of the present invention, when the patient wears the equipment, one eye is positioned at the first opening forward of the half mirror along the light axis of the video camera, and the other eye is positioned at the second opening forward of the mirror along the light axis in parallel with the light axis of the video camera. One light source illuminates one eye, and the light reflected from the eye enters the light receiving surface of the video camera after having passed through the half mirror. The other light source illuminates the other eye, and the light reflected from the eye enters the light receiving surface after having been reflected from the mirror and the half mirror in that order. The optical lens corrects an optical error arising from a difference between the two optical paths connecting between the eyes and the light receiving surface of the video camera, i.e., a difference in the size of the images formed on the light receiving surface of the video camera. The video camera converts the light received by the light receiving surface into a video signal, and the thus converted signal is output. The eye is exposed to stimulating light by activating the eye stimulating light source of the binocular optical image pick-up equipment.

By virtue of the binocular image pick-up system as defined in the sixth aspect of the present invention, the eye illuminating light source drive means activates the eye stimulating light source in response to the instruction from the light intensity instructing means. Similar to the binocular optical image pick-up system as defined in the second aspect of the present invention, the video camera alternately outputs image signals of the right and left eyes.

By virtue of the binocular optical image pick-up equipment as defined in the seventh aspect of the present invention, one eye is exposed to the stimulating light originated from the eye stimulating light source via the half mirror. Both eyes similarly react as a result of so-called light reaction.

Similar to the binocular image pick-up system as defined in the sixth aspect, by virtue of the binocular image pick-up system as defined in the eighth aspect of the present invention, the eye illuminating light source drive means activates the eye stimulating light source in response to the instruction from the light intensity instructing means. As a consequence, the eye is exposed to the stimulating light in accordance with the instruction of the light intensity instruction means. Similar to the binocular image pick-up system as defined in the second aspect, the video signals of the right and left eyes are alternately output from the video camera.

BRIEF DESCRIPTION OF THE DRAWINGS

FIGS. 4A to 4D are timing charts for illustrating the operation of the binocular optical image pick-up equipment;

DETAILED DESCRIPTION OF THE PREFERRED EMBODIMENTS

Figure 1:
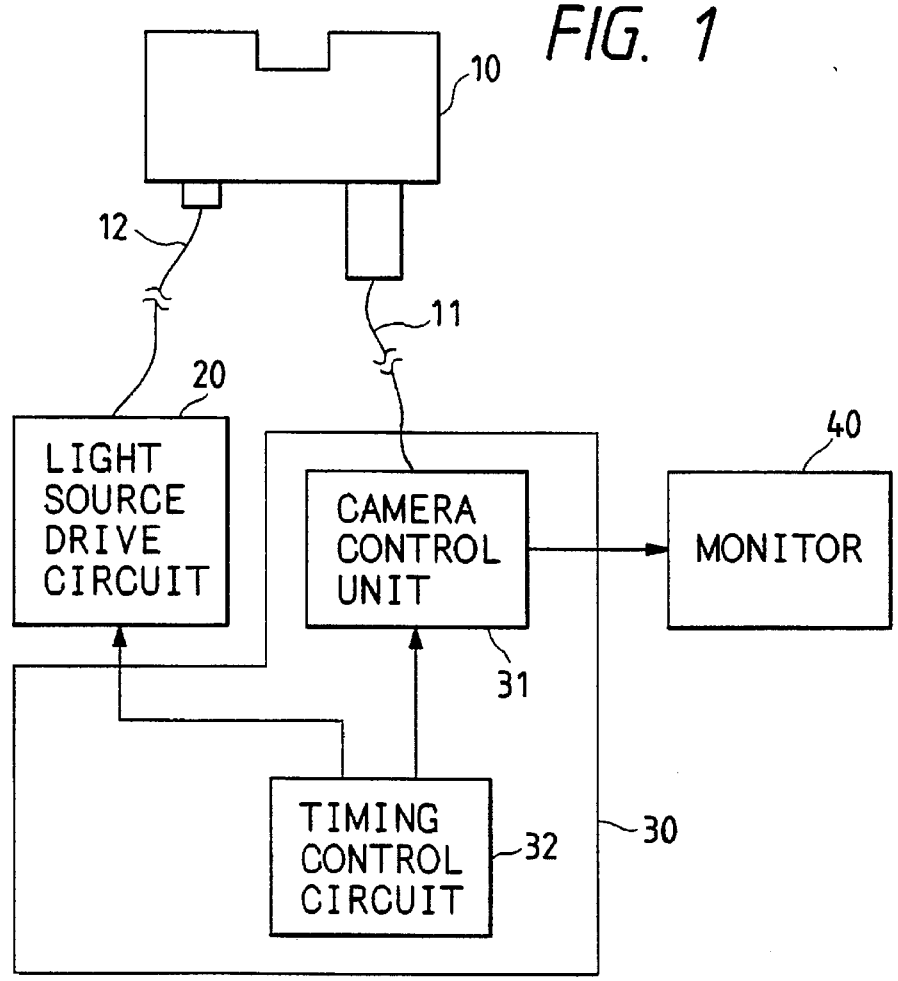
FIG. 1 is a block diagram showing the overall configuration of a binocular image pick-up system according to a first embodiment of the present invention.
Figure 2:
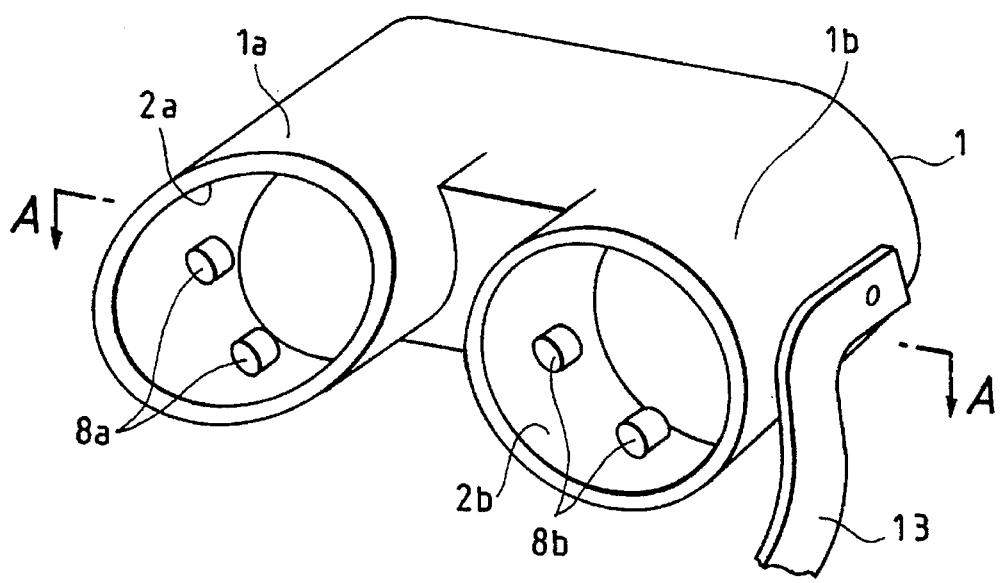
FIG. 2 is an external view of binocular optical image pick-up equipment shown in FIG. 1.
Figure 3:
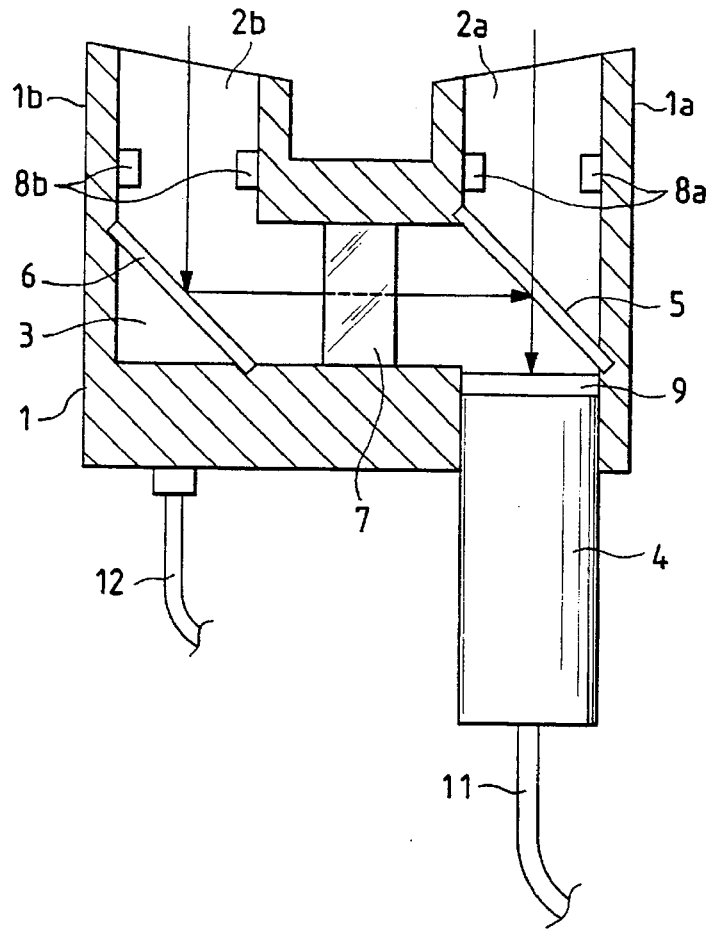
FIG. 3 is a cross-sectional view of the binocular optical image pick-up equipment taken along line A—A shown in FIG. 2.

FIG. 1 shows the overall configuration of a binocular image pick-up system according to one embodiment of the present invention. The binocular image pick-up system is made up of image pick-up optical equipment 10, a light source drive circuit 20, video camera control means 30, and a monitor 40. The image pick-up optical equipment 10, the light source drive circuit 20, and the video camera control means 30 form an image pick-up unit. FIG. 2 shows the outline of the image pick-up optical equipment 10. FIG. 3 shows a cross section of the image pick-up optical equipment taken along line A—A show in FIG. 2. The image pick-up optical equipment 10 of the present embodiment is goggles which the patient wears.

To begin with, the image pick-up equipment 10 which is shown in FIGS. 2 and 3 in a detailed manner will be described. A housing 1 has a C-shaped hollow section 3, and the hollow section 3 has two openings 2a and 2b formed on the rear side thereof. The openings 2a and 2b are spaced at an interval which is the same as the mean interval between the eyes of the patient. The periphery of the openings 2a and 2b formed on the rear side of the housing 1 cylindrically project to the outside, thereby forming cylindrical portions 1a and 1b. An aperture for communication with the outside is formed in the hollow section 3 so as to oppose the opening 2a. The video camera 4 is fitted into the aperture in such a way that the front side of the video camera faces the inside of the housing 1. The light axis of the video camera 4 is aligned with the substantial center of the opening 2a. The video camera 4 is a CCD camera.

In the hollow section 3 of the housing 1, a half mirror 5 is fixedly disposed in front of the video camera at an angle of 45° with respect to the light axis of the video camera. A mirror 6 is further fixedly disposed in the hollow section 3 of the housing 1. The mirror 6 is disposed at an angle of 45° with respect to the direction parallel to the light axis of the video camera 4 so as to reflect the light entering the opening 2b in the direction parallel with the light axis of the video camera 4 toward the half mirror 5.

An optical lens 7 is disposed between the mirror 6 and the half mirror 5. The optical lens 7 is intended to correct an optical error arising from a difference in the lengths of an optical path entering the light receiving surface of the video camera 4 from the opening 2a via the half mirror 5 and an optical path entering the light receiving surface of the video camera 4 from the opening 2b via the mirror 6 and the half mirror 5. Specifically, the optical lens 7 corrects a difference in size of images formed on the light receiving surface of the video camera.

Light sources 8a are provided along the internal circumferential surface of the hollow section 3 between the opening 2a and the half mirror 5 so as to illuminate the opening 2a. The light sources 8a are made up of four LEDs which emit infrared rays. They are circumferentially disposed at even along the internal wall surface of the housing 1. Similarly, light sources 8b are provided between the opening 2b and the mirror 6 so as to illuminate the openings 2b. The light sources 8b are made up of four LEDs which emit infrared rays. They are circumferentially disposed at even along the internal wall surface of the housing 1. In the present embodiment, the housing 1 is a support member.

A visible light cut-off filter 9 is attached to the light receiving surface of the video camera 4. Lead wires 11 coming out of the rear surface of the video camera are tied into a bundle. Lead wires 12 of the light sources 8a and 8b are wired in such a way that their leading ends are connected to the respective light sources 8a and 8b within the housing 1. The lead wires 12 are tied into a bundle outside the housing 1. The housing 1 is provided with a head band 13.

As shown in FIG. 1, the lead wires 11 of the video camera 4 are connected to the video camera control means 30, whereas the lead wires 12 of the light sources 8a and 8b are connected to the light source drive circuit 20 which activates the light sources. The video camera control means 30 is made up of a camera control unit 31 and a timing control circuit 32.

The camera control unit 31 sets an exposure time and an exposure cycle of the video camera 4. A synchronizing signal is fed to an external sync. terminal output of the video camera 4, whereby a composite video signal is formed.

The timing control circuit 32 outputs a control signal with predetermined timing to the light source drive circuit 20 and the camera control unit 31.

The monitor 40 reproduces and displays images of the respective right and left eyes from the composite video signals output from the camera control unit 31, as well as recording the thus displayed images.

In the present embodiment, the housing 1 is equivalent to the support member.

The operation of the binocular image pick-up system having the above described configuration will be described hereinbelow. To begin with, a patient wears the image pick-up optical equipment 10 on his/her face with the head band 13. The eyes are put into the openings 2a and 2b of the housing 1, so that the brims of the openings come into close contact with the surroundings of the eyes of the patient.

Figure 4D:
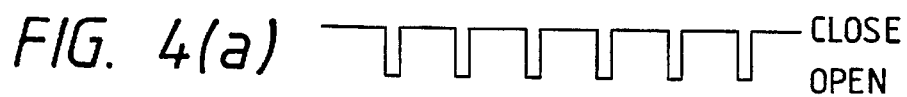
Figure 4D:
Figure 4D:
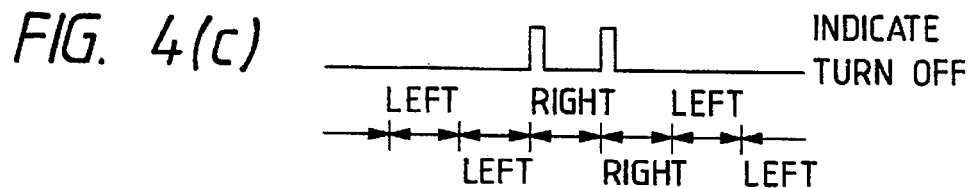
Figure 4D:
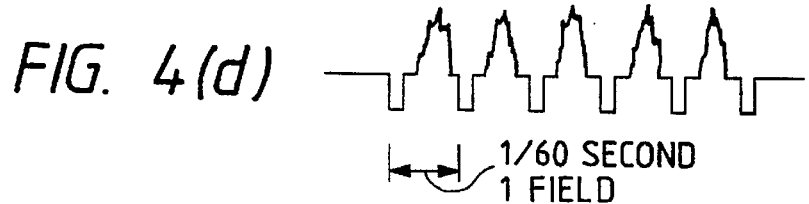

When an operator turns on the power of the binocular image pick-up system, the camera control unit 31 opens and closes an electronic shutter of the video camera 4 with timing shown in FIG. 4a under the control of the timing control circuit 32. On the other hand, the light source drive circuit 20 activates the light sources 8a with timing shown in FIG. 4b under the control of the timing control circuit 32, as well as activating the light sources 8b with timing shown in FIG. 4c. With this arrangement, the right eye is not exposed to any light at all while the left eye is exposed to the light. On the other hand, the left eye is not exposed to any light at all while the right eye is exposed to the light. Consequently, the video signals of the right and left eyes are alternately output from the video camera 4, as shown in FIG. 4d. In the present embodiment, one image (i.e., one frame) is formed by two fields. The eye acquired through the opening 2b is positioned distant from the light receiving surface of the video camera 4 compared with the eye acquired through the opening 2a by the length of an optical path between the mirror 6 and the half mirror 5. For this reason, the image formed on the light receiving surface of the video camera 4 through the opening 2b becomes smaller, and a difference in size of the images formed through the openings 2a and 2b is corrected by the optical lens 7 (a magnifying lens in the present embodiment) such that both images become identical with each other in size. If the optical lens 7 is disposed in the optical path between the opening 2a and the half mirror 5, a reducing lens is used as the optical lens 7.

The monitor 40 reproduces and displays the image of each of the right and left eyes by separating the video signal of the left eye from the video signal of the right eye, the two signals being alternately input to the monitor 40, as well as recording the thus displayed images.

The binocular optical image pick-up equipment is formed into goggles in the present embodiment, and hence it is very easy for the patient to wear.

Figure 5:
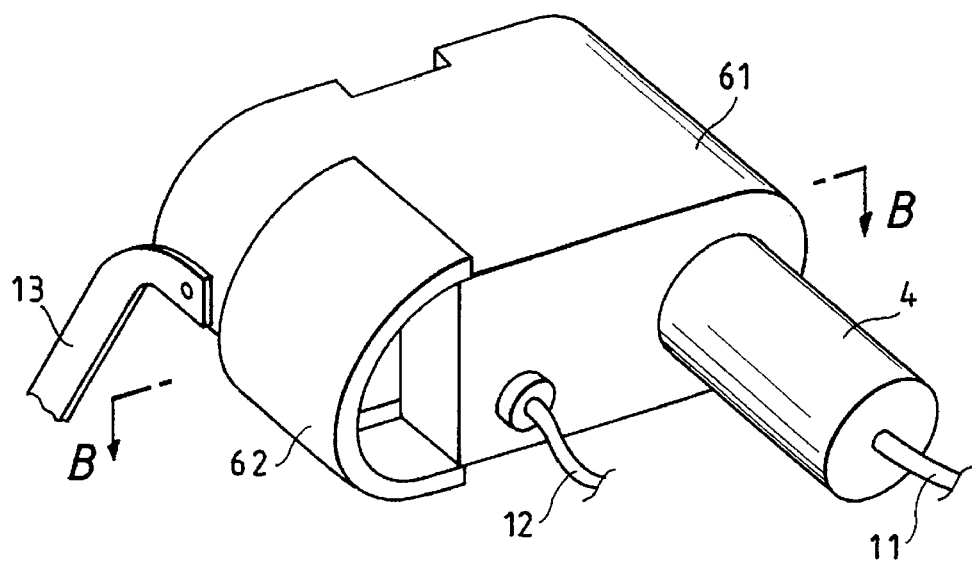
FIG. 5 is an external view of the binocular optical image pick-up equipment according to a second embodiment of the present invention.
Figure 6:
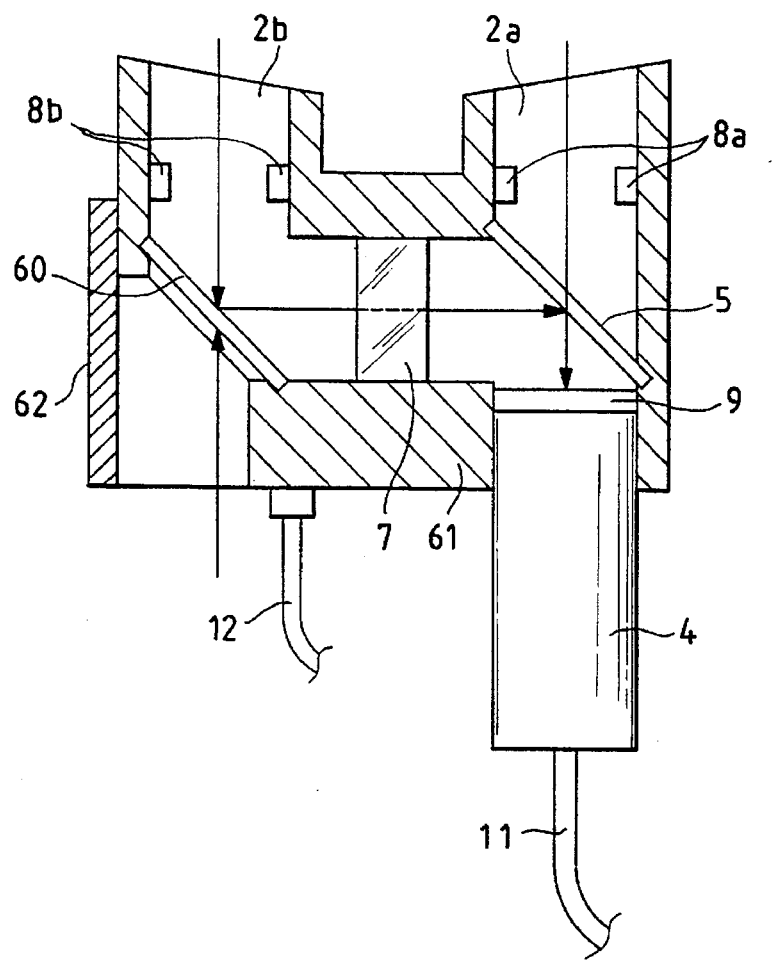
FIG. 6 is a cross-sectional view of the binocular optical image pick-up equipment taken along line B—B shown in FIG. 5.

Binocular optical image pick-up equipment according to a second embodiment of the present invention will now be described. The binocular optical image pick-up equipment according to the first embodiment of the present invention is designed so as to expose both eyes to an infrared ray for photographing purposes, whereby both eyes are photographed while they are opened in darkness. Differing from the equipment of the first embodiment, the equipment of the second embodiment is designed so as to make it possible to provide the eyes with optical stimulation, i.e., so-called patterned stimulation, from outside the goggles worn by the patient. Specifically, the eye is provided with stimulation from outside the goggles, so that the pupil contracts. The time which is necessary for the pupil to return to its original size is measured for the diagnosis of autonomic disease. Further, the equipment is capable of carrying out an optokinetic nystagmus test for observing the reaction of the patient who is sitting at the center of a rotating drum having stripes drawn on the internal circumference thereof. As can be seen from the outline view of the equipment shown in FIG. 5 and a cross sectional view thereof shown in FIG. 6 which is taken along line B—B shown in FIG. 5, the equipment of the second embodiment is different from the equipment of the first embodiment in the following points:

- the mirror 6 of the first embodiment is replaced with a half mirror 60;
- an opening is formed in the vicinity of a half mirror 60 of a housing 61 which is equivalent to the housing 1 of the first embodiment;
- light entering from the opening passes through the half mirror 60 and enters one eye of the patient; and
- a black shield plate 62 is disposed in the vicinity of the opening, as shown in the outline view of FIG. 5, for shielding external light other than the light that enters one eye of the patient via the half mirror 60 from outside. The equipment of the second embodiment is the same as the equipment of the first embodiment other than the above elements, and hence the explanation of the identical elements will be omitted here. In the second embodiment, the housing 61 is equivalent to the support member, and the cover is made up of the housing 61 and the shield plate 62.

The binocular optical image pick-up equipment having the above described construction makes it possible for the patient wearing this equipment to see outside with one eye. Further, the equipment makes it possible to observe the reaction of the pupil to optical stimulation by illuminating the eye from outside. If the pupil diameter is measured by dropping a pupil dilating agent into the eye, it becomes possible to expose the pupil to light having a desired luminous intensity before the agent is dropped into the eye, as a result of which the pupil can be reduced to a desired size. Eventually, the pupil dilates from the desired size after the agent has been dropped into the eye. The equipment of the present embodiment makes it possible to increase the degree of dilation of the pupil. As a result, it becomes possible to accurately measure changes in the pupil diameter. If the changes in the pupil diameter are measured without exposing the eye to the light, the pupil has already dilated before the pupil dilating agent is dropped into the eye. Therefore, even if the pupil dilates as a result of the dropping of the pupil dilating agent into the eye, the resultant degree of change of the pupil diameter will be small, which makes it considerably difficult to measure the changes in the pupil diameter.

Although one eye is exposed to stimulating light originated from outside in the second embodiment, the pupils of both eyes simultaneously change in the same manner for reasons of so-called light reaction. Therefore, the construction of the equipment of the second embodiment will not pose any particular problems when measuring changes in the pupil diameter.

Figure 7:
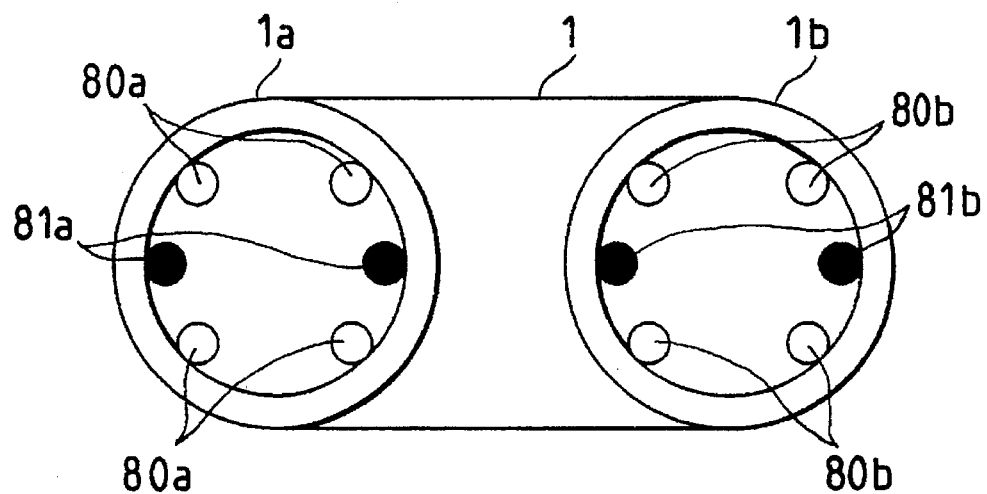
FIG. 7 is a rear view of binocular optical image pick-up equipment according to a third embodiment of the present invention.

Binocular optical image pick-up equipment according to a third embodiment of the present invention will now be described. As shown in FIG. 7, the equipment of the present embodiment is different from the equipment of the first embodiment in that eye stimulating light sources 81a and 81b for use in diagnosing autonomic disease, as being used in the second embodiment, are provided in addition to light sources 80a and 80b which are equivalent to the light sources 8a and 8b for photographing purposes of the first embodiment. The light source pairs 81a and 81b are disposed along the internal surface of the respective cylindrical portions 1a and 1b so as to oppose to each other. The equipment of the present embodiment is further provided with a drive circuit (not shown) for driving the light sources 81a and 81b, and an operation section (not shown) connected to the drive circuit. The light intensity of each of the light sources 81a and 81b is controlled by operation of the operation section. A high intensity lamp in red, white, or another color should preferably be used as the light sources 81a and 81b. Other than the above described constituent elements, the equipment of the third embodiment is the same as the equipment of the first embodiment, and hence the explanation of the other elements will be omitted here. In the present embodiment, the housing 1 is equivalent to the cover.

As with the second embodiment, it is possible to expose the eyes of the patient to light having a desired luminous intensity in the present embodiment, which makes it possible to reduce the pupil diameter to a desired size. The pupil dilates from the desired size after the pupil dilating agent has been dropped into the eye. The equipment of the present embodiment makes it possible to increase the degree of the dilation to a much greater extent, which makes it possible to accurately measure changes in the pupil diameter.

Figure 8:
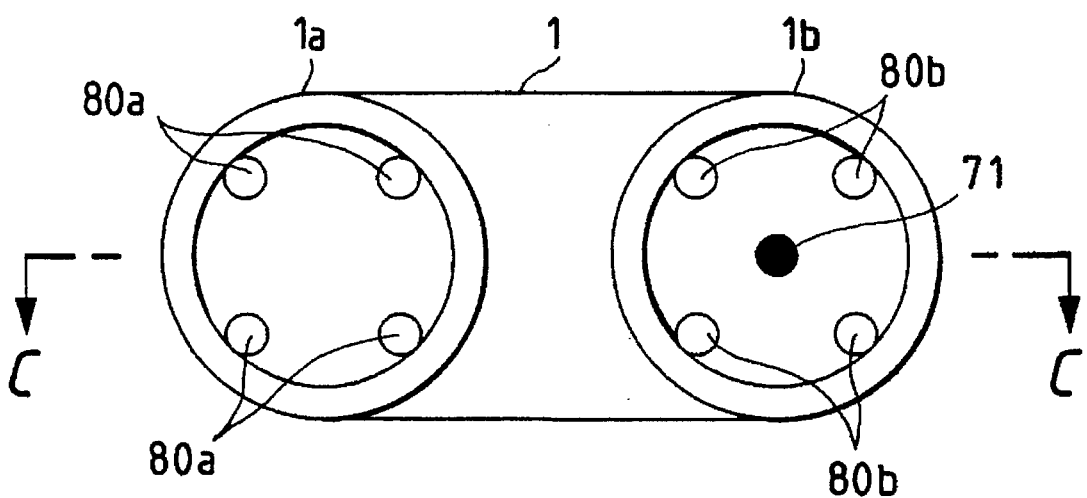
FIG. 8 is rear view of a binocular optical image pick-up equipment according to a modified example of the third embodiment.
Figure 9:
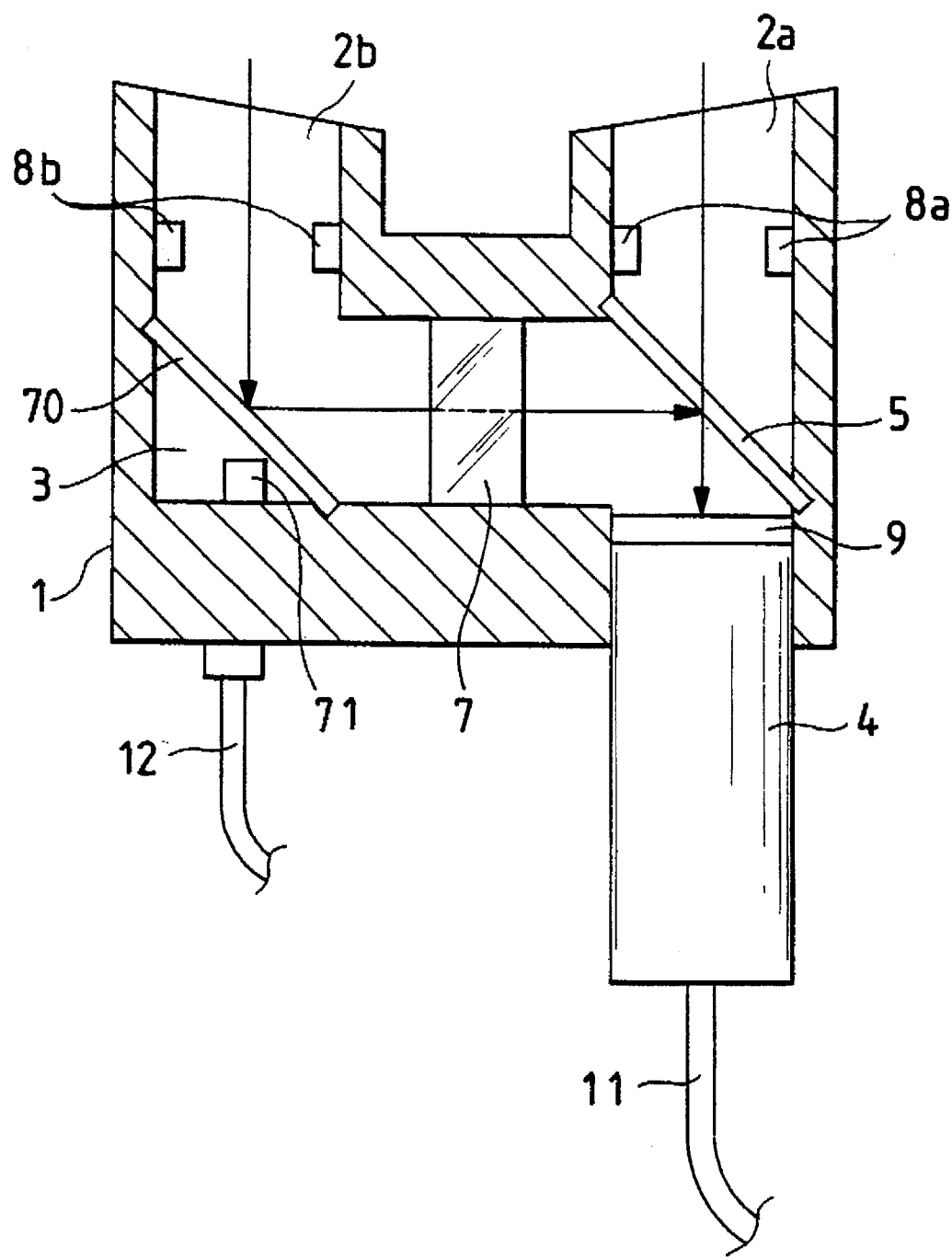
FIG. 9 is a cross-sectional view of the binocular optical image pick-up equipment taken along line C—C shown in FIG. 8.

A modified example of the third embodiment will now be described. As shown in FIGS. 8 and 9, differing from the equipment of the third embodiment, the equipment of this example is provided with a half mirror 70 instead of the mirror 6 of the third embodiment and an eye stimulating light source 71 which is attached to the housing 1 behind the half mirror 70 in line with the center axis of the cylindrical portion 1b. Effects and results similar to the results obtained by the third embodiment will be obtained by the modified example. In this example, the eye stimulating light source 71 illuminates only one eye. However, as previously described in the second embodiment, the pupils of both eyes simultaneously change in the same manner for reasons of so-called light reaction. The equipment having such a construction will not pose any particular problems when measuring the pupil diameter.

The equipment of each of the embodiments is applicable not only to the measurement of the pupil diameter but also to other measurements, e.g., the measurement of eye movement. The eye movement was conventionally measured by use of CCD cameras for use with the respective left and right eyes. The horizontal, vertical, and torsional components of the movement of each of the eyes are measured by analyzing images obtained by the two cameras. If the equipment of the above embodiments is used for the measurement, it becomes possible to measure three components of each of the eyes using only one CCD camera. Further, thirty frames are conventionally photographed per second with respect to an image of each of the left and right eyes. Contrary to this, fifteen frames are photographed per second with respect to an image of each of the left and right eyes in the above embodiments. For this reason, image data obtained by the equipment of the present embodiments will become rougher than image data obtained by the conventional equipment. However, the equipment of the above described embodiments will be sufficiently applicable for roughly measuring the eye movement or measuring slow eye movement.

According to the present invention, of several means forming the binocular image pick-up system, an optical element which is used in close proximity to the patient can be reduced in size and weight. As a result, it becomes possible for the patient to use the optical element over a long period of time while wearing it, and it is possible to acquire images of the eyes over a long period of time.

According to the present invention, it is possible to constitute an inexpensive, compact, and light-weight binocular image pick-up equipment.

According to the present invention, it is possible for the patient to see outside while wearing the equipment. Further, the eyes of the patient can be exposed to the eye stimulating light from outside. The pupil diameter of the patient can be reduced to a desirable smaller size so long as the luminous intensity of the stimulating light is appropriately controlled.

According to the present invention, it is possible to reduce the pupil diameter of the patient to a desired smaller size before the pupil dilating agent is dropped into the eyes. Eventually, it is possible to reproduce an image of the pupil having a large degree of dilation from the output of the video camera obtained after the pupil dilating agent has been dropped into the eyes. It becomes possible to accurately measure changes in the pupil diameter.

According to the present invention, the patient's eyes can be exposed to the eye stimulating light. The pupil diameter of the patient can be reduced to a desirable smaller size so long as the luminous intensity of the stimulating light is appropriately controlled.

According to the present invention, the pupil diameter of the patient can be reduced to a desirable smaller size before the pupil dilating agent is dropped into the eyes. Eventually, it is possible to reproduce an image of the pupil having a large degree of dilation from the output of the video camera obtained after the pupil dilating agent has been dropped into the eyes. It becomes possible to accurately measure changes in the pupil diameter.

According to the present invention, the binocular optical image pick-up equipment requires only one eye stimulating light source, which renders the construction of the equipment simple. Eventually, the equipment becomes easy to manufacture.

According to the present invention, the binocular optical image pick-up equipment requires only one eye stimulating light source, and hence the drive circuit for driving the eye stimulating light source becomes simple. Consequently, the overall structure of the binocular image pick-up system including the binocular optical image pick-up equipment becomes simple, and the system becomes easy to manufacture.

What is claimed is:

1. A binocular optical image pick-up equipment comprising:

a pair of light sources;

a support member for supporting the pair of light sources;

a video camera disposed close to one of the pair of light sources attached to the support member;

a mirror disposed close to the other one of the light sources for reflecting light entering in parallel with the light axis of the video camera so as to travel forward of a front light-receiving surface of the video camera;

a half mirror disposed forward of the video camera which permits light entering along the light axis of the video camera to transmit but reflects the light reflected from the mirror so as to enter the light receiving-surface of the video camera; and one of a magnifying and reducing lens disposed in at least one of an optical path which enters the half mirror from a forward position at a predetermined distance in parallel with the light axis of the video camera and an optical path which enters the mirror from a forward position at a predetermined distance along the optical axis in parallel with the light axis of the video camera and then enters the half mirror, the magnifying or reducing lens correcting a difference in the size of images formed on the light receiving surface of the video camera which arises from a difference in length between the optical paths.

2. A binocular image pick-up system as claimed in claim 1, further comprising:

light source drive means for driving the pair of light sources; and video camera control means for alternately illuminating the pair of light sources by activating the light source drive means, as well as for controlling the video camera in synchronism with the periodicity of the illumination.

3. A binocular image pick-up system as claimed in claim 1, further comprising:

a first opening for transmitting light entering forward of the video camera and the half mirror along the light axis of the video camera;

a second opening for transmitting light entering forward of the mirror along the optical axis in parallel with the light axis of the video camera;

a cover for preventing the entry of external light into the two optical paths from outside other than through the first and second openings; and an eye stimulating light source disposed in the cover so as to illuminate at least one of the first and second openings.

4. A binocular image pick-up system as claimed in claim 3, further comprising:

light intensity instructing means for instructing the intensity of the light originated from the eye illuminating light source;

eye illuminating light source drive means for activating the eye stimulating light source in response to an instruction from the light intensity instructing means;

photographing light source drive means for activating the pair of light sources; and video camera control means for alternately illuminating the pair of light sources by activating the light source drive means, as well as for controlling the video camera in synchronism with the periodicity of the illumination.

5. The binocular image pick-up system as claimed in claim 4, wherein the mirror is a half mirror, and the eye stimulating light source is positioned behind the half mirror in parallel with the light axis of the video camera.

6. The binocular optical image pick-up equipment as claimed in claim 3, wherein the mirror is a half mirror, and the eye stimulating light source is positioned behind the half mirror with respect to the second opening.

7. Binocular optical image pick-up equipment comprising:

- a pair of light sources;
- a support member for supporting the pair of light sources;
- a video camera disposed close to one of the pair of light sources and attached to the support member;
- a first half mirror disposed close to the other one of the light sources for reflecting light entering in parallel with the light axis of the video camera so as to travel forward of a front light-receiving surface of the video camera as well as for permitting the transmission of light entering from the direction opposite to the direction of the light to be reflected;
- a second half mirror disposed forward of the video camera which permits the transmission of light entering along the light axis of the video camera but reflects the light reflected from the first half mirror so as to enter the light receiving-surface of the video camera;
- one of a magnifying and reducing lens disposed in at least one of an optical path which enters the half mirror from a forward position at a predetermined distance in parallel with the light axis of the video camera and an optical path which enters the mirror from a forward position at a predetermined distance along the optical axis in parallel with the light axis of the video camera and then enters the half mirror, the magnifying or reducing lens correcting a difference in the size of images formed on the light receiving surface of the video camera which arises from a difference in length between the optical paths;
- a first opening for transmitting light entering forward of the video camera and the second half mirror along the light axis of the video camera;
- a second opening for transmitting light entering forward of the first half mirror along the optical axis in parallel with the light axis of the video camera;
- a third opening for transmitting light so as to enter the first half mirror from the rear side thereof; and
- a cover for preventing the entry of external light into the two optical paths and the optical path connecting between the third opening and the first half mirror from outside other than the first through third openings.

8. A binocular image pick-up system as claimed in claim 7, further comprising:

- light source drive means for driving the pair of light sources; and
- video camera control means for alternately illuminating the pair of light sources by activating the light source drive means, as well as for controlling the video camera in synchronism with the periodicity of the illumination.

* * * * *